(12) United States Patent
Yamazaki et al.

(10) Patent No.: US 10,371,592 B2
(45) Date of Patent: Aug. 6, 2019

(54) SYSTEM STABILITY MONITORING APPARATUS AND METHOD

(71) Applicant: Hitachi, Ltd., Tokyo (JP)

(72) Inventors: Jun Yamazaki, Tokyo (JP); Masahiro Yatsu, Tokyo (JP); Sumito Tobe, Tokyo (JP); Yasuo Sato, Tokyo (JP); Osamu Tomobe, Tokyo (JP); Eisuke Kuroda, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 310 days.

(21) Appl. No.: 15/127,822

(22) PCT Filed: Sep. 19, 2014

(86) PCT No.: PCT/JP2014/074776
§ 371 (c)(1),
(2) Date: Sep. 21, 2016

(87) PCT Pub. No.: WO2015/151316
PCT Pub. Date: Oct. 8, 2015

(65) Prior Publication Data
US 2017/0097271 A1    Apr. 6, 2017

(30) Foreign Application Priority Data
Mar. 31, 2014 (JP) .................. 2014-070833

(51) Int. Cl.
*G01M 1/14* (2006.01)
*H02S 50/10* (2014.01)
(Continued)

(52) U.S. Cl.
CPC ............... *G01M 1/14* (2013.01); *G01N 29/11* (2013.01); *G01N 29/12* (2013.01);
(Continued)

(58) Field of Classification Search
CPC .......... G01M 1/14; H02S 50/00; H02S 50/10; H02J 3/383; H02J 3/386; H02J 3/1821;
(Continued)

(56) References Cited

U.S. PATENT DOCUMENTS 9,876,352 B2 * 1/2018 Biswas .................... H02J 3/00
2009/0240382 A1 * 9/2009 Mitani .................... H02J 3/24
700/298
(Continued)

FOREIGN PATENT DOCUMENTS

JP    07-99742 A    4/1995
JP    2001-352679 A    12/2001
(Continued)

OTHER PUBLICATIONS

International Search Report of PCT/JP2014/074776 dated Nov. 11, 2014.

*Primary Examiner* — Manuel L Barbee
(74) *Attorney, Agent, or Firm* — Mattingly & Malur, PC (57) ABSTRACT

When vibration information calculated using measurement information is classified using a distance between measurement points which is calculated using the point information, even in a case in which a plurality of vibration modes with close vibration frequencies are present at the same time, stability determination at a high speed and a high accuracy is realized. A system stability monitoring apparatus which monitors system stability of a power system includes a measurement information collecting unit that collects measurement information of a plurality of points in the power system, a vibration analyzing unit that calculates vibration information indicating vibration of a system state in the plurality of points using the measurement information, an information storage unit that stores point information including position information of the plurality of points, and a
(Continued)

vibration classifying unit that classifies the vibration information based on the point information.

13 Claims, 7 Drawing Sheets

(51) Int. Cl.
| | | |
|---|---|---|
| *H02J 3/38* | (2006.01) | |
| *G01N 29/48* | (2006.01) | |
| *H02J 50/20* | (2016.01) | |
| *G01N 29/11* | (2006.01) | |
| *G01N 29/12* | (2006.01) | |
| *G01N 29/44* | (2006.01) | |
| *H02S 50/00* | (2014.01) | |
| *H02J 13/00* | (2006.01) | |
| *H02J 3/18* | (2006.01) | |

(52) U.S. Cl.
CPC ......... *G01N 29/4445* (2013.01); *G01N 29/48* (2013.01); *H02J 3/383* (2013.01); *H02J 3/386* (2013.01); *H02J 13/001* (2013.01); *H02J 13/0086* (2013.01); *H02J 50/20* (2016.02); *H02S 50/00* (2013.01); *H02S 50/10* (2014.12); *H02J 3/1821* (2013.01); *Y02E 10/563* (2013.01); *Y02E 10/763* (2013.01); *Y02E 40/30* (2013.01); *Y02E 40/72* (2013.01); *Y04S 10/123* (2013.01); *Y04S 10/40* (2013.01)

(58) Field of Classification Search
CPC ... H02J 13/001; H02J 13/0086; Y02E 10/563; Y02E 10/763; Y02E 40/30; Y02E 40/72; Y04S 10/123; Y04S 10/40
See application file for complete search history.

(56) References Cited

U.S. PATENT DOCUMENTS

2009/0307233 A1* 12/2009 Zhang ............... G06F 17/30516
2013/0345999 A1* 12/2013 Hafen ................. G01R 21/133
702/60

FOREIGN PATENT DOCUMENTS

| JP | 2009-077589 | 4/2009 |
| JP | 2013-219853 A | 10/2013 |

* cited by examiner

| NAME OF VIBRATION MEASUREMENT POINT | No. | VIBRATION FREQUENCY | ATTENUATION COEFFICIENT | AMPLITUDE | INITIAL PHASE |
|---|---|---|---|---|---|
| PMU1 | 1 | 0.18 | -2.0 | 120 | 10 |
| PMU1 | 2 | 0.65 | -0.5 | 80 | 30 |
| ⋮ | ⋮ | ⋮ | ⋮ | ⋮ | ⋮ |
| PMU2 | 1 | 0.19 | -1.9 | 90 | 15 |
| ⋮ | ⋮ | ⋮ | ⋮ | ⋮ | ⋮ |

(b)

| VIBRATION FREQUENCY | NAME OF VIBRATION MEASUREMENT POINT | No. | ATTENUATION COEFFICIENT | AMPLITUDE | INITIAL PHASE |
|---|---|---|---|---|---|
| 0.18 | PMU1 | 1 | -2.0 | 120 | 10 |
| 0.18 | PMU2 | 1 | -1.9 | 90 | 15 |
| | ⋮ | ⋮ | ⋮ | ⋮ | ⋮ |
| 0.65 | PMU1 | 2 | -0.5 | 80 | 30 |
| ⋮ | ⋮ | ⋮ | ⋮ | ⋮ | ⋮ |

(c)

| VIBRATION No. | VIBRATION FREQUENCY | MEASUREMENT POINT | ATTENUATION COEFFICIENT | AMPLITUDE | INITIAL PHASE |
|---|---|---|---|---|---|
| 1 | 0.18 | PMU1 | -2.0 | 120 | 10 |
| 1 | 0.18 | PMU3 | -1.0 | 30 | -10 |
| | | ⋮ | ⋮ | ⋮ | ⋮ |
| 2 | 0.65 | PMU1 | -0.5 | 80 | 30 |
| | | ⋮ | ⋮ | ⋮ | ⋮ |
| 3 | 0.18 | PMU2 | -1.9 | 90 | 15 |
| | | ⋮ | ⋮ | ⋮ | ⋮ |

| NAME OF NODE | POSITION INFORMATION | | POWER GENERATOR | | | LOAD | | | PHASE MODIFIER | | |
|---|---|---|---|---|---|---|---|---|---|---|---|
| | LATITUDE | LONGITUDE | NAME | TYPE | RATING CAPACITY | NAME | TYPE | RATING CAPACITY | NAME | TYPE | RATING CAPACITY |
| A | 36.5 | 138.2 | G1 | THERMAL POWER | 100 | ... | ... | ... | ... | ... | ... |
| B | 37.7 | 140.5 | G2 | HYDROELECTRIC POWER | 200 | ... | ... | ... | ... | ... | ... |
| ... | ... | ... | ... | ... | ... | ... | ... | ... | ... | ... | ... |
| AA | 35.7 | 139.8 | ... | ... | ... | L1 | HOUSING | 1000 | ... | ... | ... |
| BB | 35.0 | 139.5 | ... | ... | ... | L2 | FACTORY | 2000 | ... | ... | ... |
| ... | ... | ... | ... | ... | ... | ... | ... | ... | ... | ... | ... |
| AAA | 36.3 | 139.0 | ... | ... | ... | ... | ... | ... | D1 | SC | 10 |
| BBB | 35.6 | 138.6 | ... | ... | ... | ... | ... | ... | D2 | ShR | 20 |
| ... | ... | ... | ... | ... | ... | ... | ... | ... | ... | ... | ... |

(b)

| NAME OF TRANSMISSION LINE | BOTH-END NODE | | POSITIVE-PHASE RESISTANCE R | POSITIVE-PHASE REACTANCE X | POSITIVE-PHASE CAPACITANCE C |
|---|---|---|---|---|---|
| a | A | B | 0.01 | 0.2 | 0.1 |
| b | B | C | 0.02 | 0.5 | 0.2 |
| ... | ... | ... | ... | ... | ... |

(c)

| MEASUREMENT POINT 1 | | MEASUREMENT POINT 2 | | DISTANCE BETWEEN MEASUREMENT POINTS |
|---|---|---|---|---|
| NAME OF MEASUREMENT POINT | NAME OF NODE | NAME OF MEASUREMENT POINT | NAME OF NODE | |
| PMU1 | A | PMU2 | B | 15 |
| PMU1 | A | PMU3 | C | 40 |
| ... | ... | ... | ... | ... |

[FIG. 8]

SYSTEM STABILITY MONITORING APPARATUS AND METHOD

TECHNICAL FIELD

The present invention relates to a system stability monitoring apparatus which monitors a system state of a power system, and a method thereof.

BACKGROUND ART

A power system is configured with many power generators, loads, transmission and distribution devices, and controllers. In a normal state, small external disturbance may be applied to the power system due to load change, system switching, or the like. At the time of the occurrence of an accident such as ground fault or short-circuiting of the system, large external disturbance is applied to the power system. This external disturbance causes generation of power vibration including a plurality of vibration mode components.

In a case in which the vibration mode components are small or attenuated at a high speed, the system vibration after the occurrence of external disturbance is maintained in a sufficiently small range, and thus the power system is in a stable state. However, in a case in which the vibration becomes large or continues or disperses instead of being attenuated, consequently, the power generator stops, or power failure occurs in a wide range, and thus there is a possibility that the stable operation becomes impossible.

Together with an increase in the size of power systems, there is a tendency of an increase of a power supply capacity, an increase of the installation distance, uneven distribution, accordingly, an increase in the length of the transmission line, and an increase of the amount of electric currents flowing in lines. Since these changes cause the stability of the power system to be deteriorated, there is a concern of an expansion of a serial influence on large scale power dropout and power failure in a wide range caused by the step-out of the power generator at the time of system failure.

Therefore, an online system stability evaluation method which constantly monitors the stability of the system, and prevents and predicts the power generator step-out, and the like in advance becomes necessary.

Recently, a phasor measurement unit (PMU) which measures a phase angle of a bus voltage of the power system on almost a real-time basis by means of synchronous measurement using GPS has become widespread. It has become possible to understand a power vibration phenomenon on a real-time basis using an online measurement value such as the bus voltage of the system, or the like measured by the phasor measurement unit PMU.

From the above described background, a system state monitoring technology for an operator who operates the power system to monitor the stability of the system state has been devised. For example, in PTL 1, a power vibration mode observing apparatus, which accurately identifies an attenuation ratio playing an important role in steady state stability evaluation using a phase angle detecting apparatus, is disclosed.

CITATION LIST

Patent Literature

PTL 1: JP-A-2009-77589

SUMMARY OF INVENTION

Technical Problem

However, when a large amount of renewable energy represented by the solar power or the wind power in the future is introduced into the system, the renewable energy accompanies an abrupt power generation output change which cannot be easily assumed in advance, and consequently, there is a possibility that a system characteristic significantly changes. For example, in a case in which the wind speed exceeds a certain threshold value, a so called cut-out operation, in which the wind power generation is automatically stopped and the power generating output becomes zero in order to maintain the safety of a device occurs. This phenomenon occurs more frequently than an accident of ground fault or short-circuiting which also occurs in systems of the related art, and, in a case in which power generators are densely installed in close regions, this phenomenon is expected to be highly likely to occur at the same time in a plurality of power generators.

As the introduction amount of the renewable energy increases, an impact on the system due to the above described abrupt output change event increases, and there is a concern that the vibration mode in a wide range may become unstable. In order to cope with this concern, high-speed and high-accuracy stability determination becomes necessary in an intermediate region of approximately several seconds to ten several seconds immediately after the output change event.

In order for high-speed stable determination, it is necessary to decrease the input data length more than in the related art. However, in a case in which input data is shortened, the influence of noise on the system vibration mode becomes relatively large, and high-accuracy detection of vibration modes becomes difficult. In addition, the frequency resolution decreases as a trade-off with the input data length due to the uncertainty principle of the Ferrier conversion, and thus it becomes difficult to separate and detect a plurality of vibration modes with close frequencies.

Therefore, in a case in which a plurality of vibration modes with close vibration frequencies are present at the same time, the plurality of vibration disappears together depending on measurement points, and there is a possibility that points at which high-accuracy detection of vibration modes becomes difficult are generated. In such a case, in the technology described in PTL 1, high-speed and high-accuracy stable determination cannot be realized.

Solution to Problem

In order to solve the above problems, according to the invention, a system stability monitoring apparatus which monitors system stability of a power system includes a measurement information collecting unit that collects measurement information of a plurality of points in the power system, a vibration analyzing unit that calculates vibration information indicating vibration of a system state in the plurality of points using the measurement information, an information storage unit that stores point information including position information of the plurality of points, and a vibration classifying unit that classifies the vibration information based on the point information.

Advantageous Effects of Invention

According to the invention, when vibration information calculated using measurement information is classified using a distance between measurement points which is calculated using the point information, even in a case in which a plurality of vibration modes with close vibration frequencies are present at the same time, a high speed and a high accuracy stable determination can be realized.

DESCRIPTION OF EMBODIMENTS

Hereinafter, examples suitable for embodiments of the invention will be described. Also, these embodiments to be described later are presented by way of example only, and it is not intended that the invention itself is limited to a specific content.

The embodiments of the invention will be described hereinafter with reference to drawings.

Example 1

Figure 1:
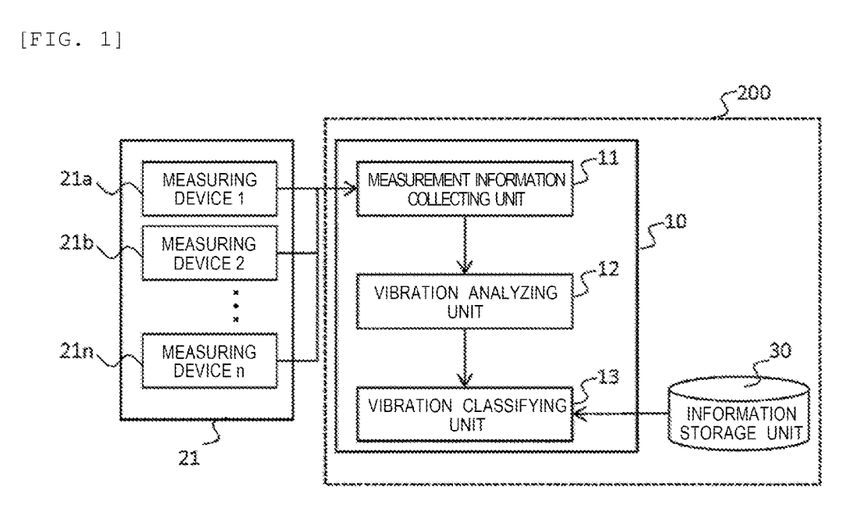
FIG. 1 is a block diagram illustrating a functional configuration of a measuring device and a system stability monitoring apparatus.

FIG. 1 illustrates a diagram of a functional configuration when a system stability monitoring apparatus to which an embodiment of the invention is applied is associated with a measuring device of a system. As illustrated in FIG. 1, a system stability monitoring apparatus 200 in the embodiment is configured with a system stability calculating unit 10 and an information storage unit 30.

The system stability calculating unit 10 is configured with a measurement information collecting unit 11, a vibration analyzing unit 12, and a vibration classifying unit 13 therein.

The measurement information collecting unit 11 collects system measurement information measured in a system measuring unit 21.

The vibration analyzing unit 12 calculates vibration information using the system measurement information collected by the measurement information collecting unit 11.

The vibration classifying unit 13 classifies the vibration information calculated in the vibration analyzing unit 12 using the point information stored in the information storage unit 30, and extracts the vibration information with high importance degree.

The system measuring unit 21 measures the system measurement information in a measurement point inside the system and transmits the information to the measurement information collecting unit 11. The system measurement information includes at least one of an active power flow, a reactive power flow, a system voltage, a system current, and a voltage phase. The system measuring unit 21 is configured with measuring devices 21a, 21b, . . . , 21n which are disposed at a plurality of measurement points.

The information storage unit 30 of a system stores the point information which indicates connection information of a system element relating to the power system. In the point information, characteristic information of a system element such as the power generator, load, or a phase modifier, which is connected to each node inside the system and information of a transmission line connecting each node to each other.

Figure 2:
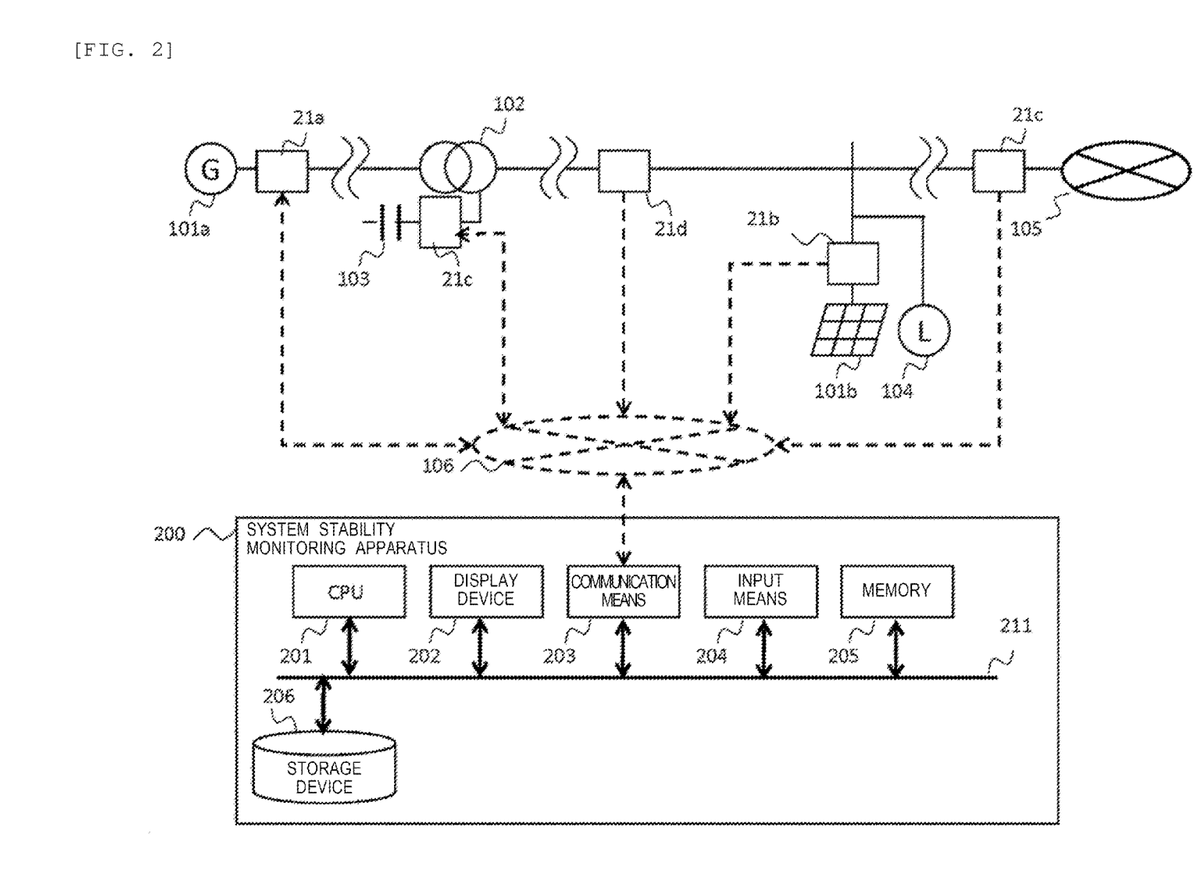
FIG. 2 is an example of an entire configuration diagram of a system stability monitoring system according to the invention.

FIG. 2 is the entire configuration diagram of the system stability monitoring system to which an embodiment of the invention is applied. As illustrated in FIG. 2, the system stability monitoring system in the embodiment is configured with a power generator 101, a substation 102, a phase modifier 103, a power load 104, an external power system 105, the measuring devices 21a and 21b, an information communication network 106, and the system stability monitoring apparatus 200.

The power generator 101 is a power generator which generates a power-generating capacity, and is a power generator which generates the power-generating capacity by any one power generating method of thermal power generation, hydroelectric power generation, nuclear power generation, the solar power generation, wind power generation, biomass power generation, and tidal power generation. The power generator 101a is a large scale power generator including the thermal power generation, the hydroelectric power generation, the nuclear power generation, or the like which is installed on a high voltage side of the power system, and transmits a system state amount including a power generating amount to the system stability monitoring apparatus 200 through the measuring device 21a and the information communication network 106. In addition, the power generator 101a receives control instruction information which is transmitted by the system stability monitoring apparatus 200 through the measuring device 21a and the information communication network 106, and changes the system state amount including the power generating amount according to the control instruction information. The power generator 101b is a small and medium scale power generator including the solar power generation, the wind power generation, cogeneration, or the like which is disposed on a low voltage side of the power system, and transmits the system state amount including the power generating amount to the system stability monitoring apparatus 200 through the measuring device 21b and the information communication network 106.

The substation 102 is provided between the transmission lines inside the power system, changes a voltage value of power transmitted by a high voltage side where the power generator 101a, which is a large scale power generator, is provided, and transmits the voltage value to the low voltage side where the power load 104 is provided. In the substation 102, the phase modifier 103 such as a power capacitor or a shunt reactor is connected.

The phase modifier 103 is equipment which controls a voltage distribution inside the power system by changing the reactive power inside the power system, and includes the power capacitor, the shunt reactor, STATCOM, SVC, or the like. A part of the phase modifier 103 receives the control instruction information which is transmitted by the system stability monitoring apparatus 200 through the measuring device 21c and the information communication network 106, and changes the system state amount including the power generating amount according to the control instruction information.

The power load 104 indicates a house, a factory, building, and facilities in which an electric motor, lighting equipment, or the like which consumes power is included.

The external power system 105 is an external power system which cannot be controlled by the system stability monitoring apparatus 200, and is connected to the system itself by an interconnection line.

The measuring devices 21a, 21b, . . . include a sensor which measures the system state amount such as the power generating amount in the power generator 101a, a phase modifying amount in the phase modifier 103, a tidal current value in the transmission line, or a voltage value, therein, and transmits the measured system state amount to the system stability monitoring apparatus 200 through the information communication network 106.

The information communication network 106 is a network which is capable of performing bidirectional transmission of data. The information communication network 106 is configured with, for example, a wired network, a wireless network, or a combination those of. The information communication network 106 may be so called Internet, or may be an excluded line network.

The system stability monitoring apparatus 200 is an apparatus for realizing a system stability monitoring function illustrated in FIG. 1. The system stability monitoring apparatus 200 receives the system state amount which is measured in the measuring device 21a, 21b, . . . through the information communication network 106. In addition, the system stability monitoring apparatus 200 transmits the control instruction information calculated using the transmitted system state amount and the information accumulated in the system through the information communication network 106 to the measuring device 21a, or the like.

As an internal configuration of the system stability monitoring apparatus 200, a central processing unit (CPU) 201, a display device 202, communication means 203, input means 204, a memory 205, and a storage device 206 are connected to a bus line 211. The CPU 201 executes a calculation program, and performs calculation of the system state, generation of a control signal, or the like. The memory 205 is a memory which temporarily stores image data for displaying, a calculation result data of the system state, or the like, and for example, is configured with a random access memory (RAM). The memory 205 generates a necessary image data by the CPU 201 and displays the data to the display device 202. The communication means 203 acquires the system state amount such as a tidal current value and a voltage value from the measuring device 21 and the measuring device 21 through a communication network 106.

A user can appropriately set an operation of the system stability monitoring apparatus 200 by setting and changing a parameter such as various thresholds through a predetermined interface of the input means 204. In addition, the user selects types of data that the user wants to recognize through the predetermined interface of the input means 204, and can displays the types of data to the display device 202.

The storage device 206 holds various program and data. The storage device 206 is configured with, for example, a hard disk drive (HDD) or a flash memory. The storage device 206 holds, for example, a program and data which are capable of realizing various functions to be described later. The program and data stored in the storage device 206 are read and executed by the CPU 201 as needed. Also, the storage device 206 is constituted by various databases DB.

Next, a first example of a system stability calculating process in the system stability monitoring apparatus 200 will be described using a flow chart illustrated in FIG. 3.

First, the vibration analyzing unit 12 calculates the vibration information using measurement information of a plurality of the points measured in the system measuring unit 21 (S31). Here, the measurement information of the plurality of points measured in the system measuring unit 21 includes at least one of information of the active power flow, the reactive power flow, the system voltage, the system current, and the voltage phase. The vibration information is calculated by at least one method of a fourier analysis, a wavelet analysis, a puroni method, a matrix pencil method, and a hankel total least squares (HTLS) method when the measurement information is set as an input.

Hereinafter, a vibration information calculation algorithm will be described by the puroni method.

The number N of data and the number n of mode order of an analysis window width are set in advance.

A matrix $a=(a_1, a_2, \ldots, a_n)^T$ is calculated using input data $y(k)$ ($k=0, 1, \ldots, N-1$) from Math. 1 to Math. 4 as follows. However, a superscript letter "T" described above indicates a transposed matrix, and a latter "−1" indicates an inverse matrix.

$$a = (X^T X)^{-1} X^T y \qquad \text{[Math. 1]}$$

$$a = \begin{bmatrix} a_1 \\ a_2 \\ \vdots \\ a_n \end{bmatrix} \qquad \text{[Math. 2]}$$

$$X = \begin{bmatrix} y(n-1) & y(n-2) & \cdots & y(0) \\ y(n) & y(n-1) & \cdots & y(1) \\ \vdots & \vdots & \ddots & \vdots \\ y(N-2) & y(N-3) & \cdots & y(N-n-1) \end{bmatrix} \qquad \text{[Math. 3]}$$

$$y = \begin{bmatrix} y(n) \\ y(n+1) \\ \vdots \\ y(N-1) \end{bmatrix} \qquad \text{[Math. 4]}$$

From Math. 1 to Math. 4, the calculated $a_1, a_2, \ldots,$ and $a_n$ are substituted in Math. 5 to be described below. $Z_i$ indicated by expressions of Math. 6 and Math. 7 is substituted in Z of Math. 5, and an eigenvalue $\lambda_i$, the attenuation coefficient $\sigma_i$ [1/sec], and a vibration frequency $f_i$ [Hz]$=\omega_i/2\pi$ are calculated. Here, $\Delta t$ indicates a sampling period.

Math. 5 is a polynomial (characteristics equation) of the n-th degree which has $Z_i$ as a solution, and n number of $Z_i$, $\sigma_i$, and $f_i$ is respectively obtained as a solution.

$$Z^n - (a_1 Z^{n-1} + a_2 Z^{n-2} + \ldots + a_n Z^0) = 0 \qquad \text{[Math. 5]}$$

$$Z_i = \exp(\lambda_i \Delta t) \qquad \text{[Math. 6]}$$

$$\lambda_i = \sigma_i + \omega_i j \qquad \text{[Math. 7]}$$

A matrix $b=(B_1, B_2, \ldots, \text{and } B_n)^T$ is calculated using input data $y(k)$ ($k=0, 1, \ldots, N-1$), and the calculated $Z_i$ ($i=1, 2, \ldots, n$) from Math. 8 to Math. 11 to be described later.

$$b = (Z^T Z)^{-1} Z^T w \quad \text{[Math. 8]}$$

$$b = \begin{bmatrix} B_1 \\ B_2 \\ \vdots \\ B_n \end{bmatrix} \quad \text{[Math. 9]}$$

$$Z = \begin{bmatrix} Z_1^0 & Z_2^0 & \cdots & Z_n^0 \\ Z_1^1 & Z_2^1 & \cdots & Z_n^1 \\ \vdots & \vdots & \ddots & \vdots \\ Z_1^{N-1} & Z_2^{N-1} & \cdots & Z_n^{N-1} \end{bmatrix} \quad \text{[Math. 10]}$$

$$w = \begin{bmatrix} y(0) \\ y(1) \\ \vdots \\ y(N-1) \end{bmatrix} \quad \text{[Math. 11]}$$

An absolute value $R_i$ and a variation angle $\theta_i$ indicated by Math. 12 are obtained from $B_1, B_2, \ldots, B_n$ calculated from Math. 8 to Math. 11. At this time, the absolute value $R_i$ means an amplitude, and the variation angle $\theta_i$ means an initial phase.

$$B_i = R_i \exp(j\theta_i) \quad \text{[Math. 12]}$$

The vibration frequency calculated by the above described process, the attenuation coefficient, an amplitude, and the initial phase are termed the vibration information.

Figure 4:
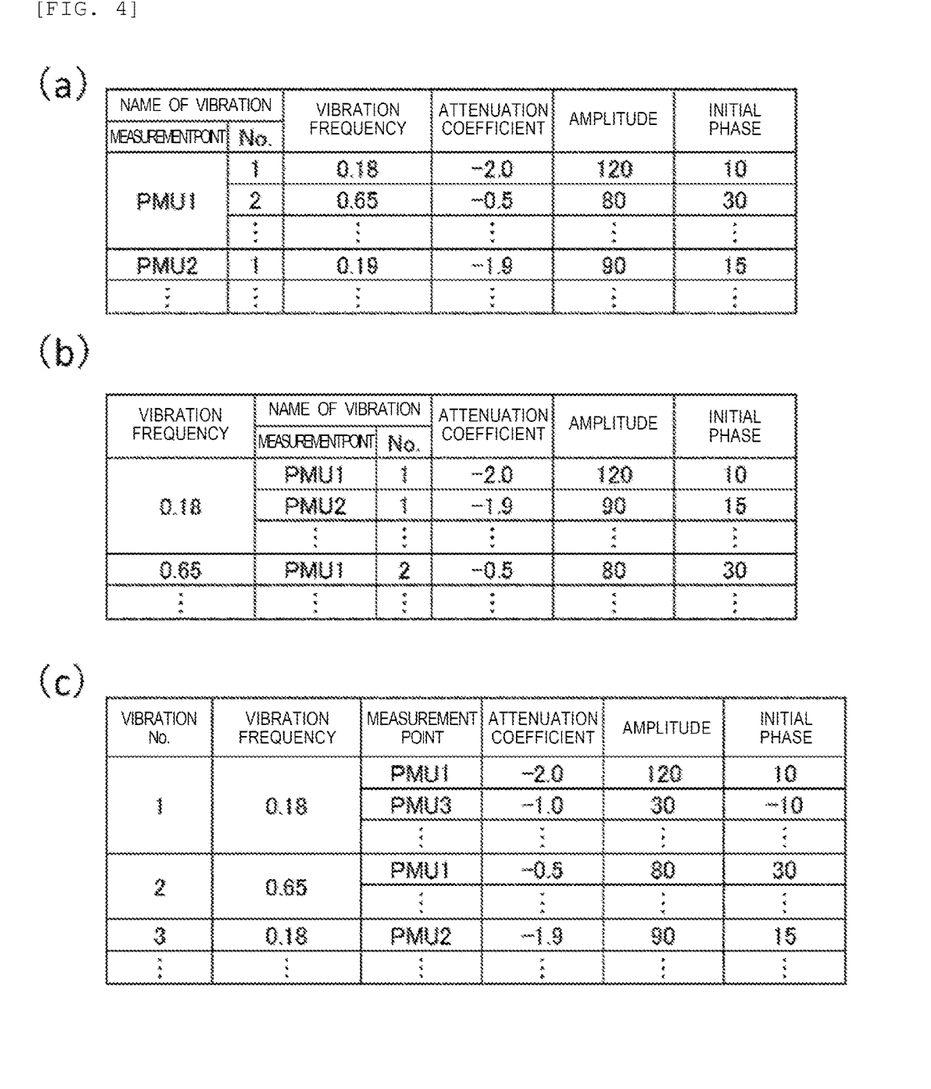
FIG. 4 is an example of a data configuration of vibration information output by the system stability monitoring apparatus.

FIG. 4(a) illustrates an example of a data configuration of the calculated vibration information. A name of vibration in FIG. 4(a) is indicated by a measurement point, where the measurement value is used as the input data, and No. In a case in which the vibration information is calculated using the puroni method, with respect to the measurement information of one type of a first measurement point which is used as the input data, the vibration information which is the same as the number n of the mode order is calculated. Accordingly, in a case in which the measurement information of a q type (q≥1) is used in each point of a p point (p≥1), n×p×q vibration information is calculated. In an example of FIG. 4(a), regarding each vibration, the vibration frequency, the attenuation coefficient, the amplitude, and the initial phase are calculated as the vibration information.

Next, based on the vibration information calculated by the vibration analyzing unit 12 and the point information stored in the information storage unit 30, the vibration classifying unit 13 clusters the plurality of points (S32).

Figure 5:
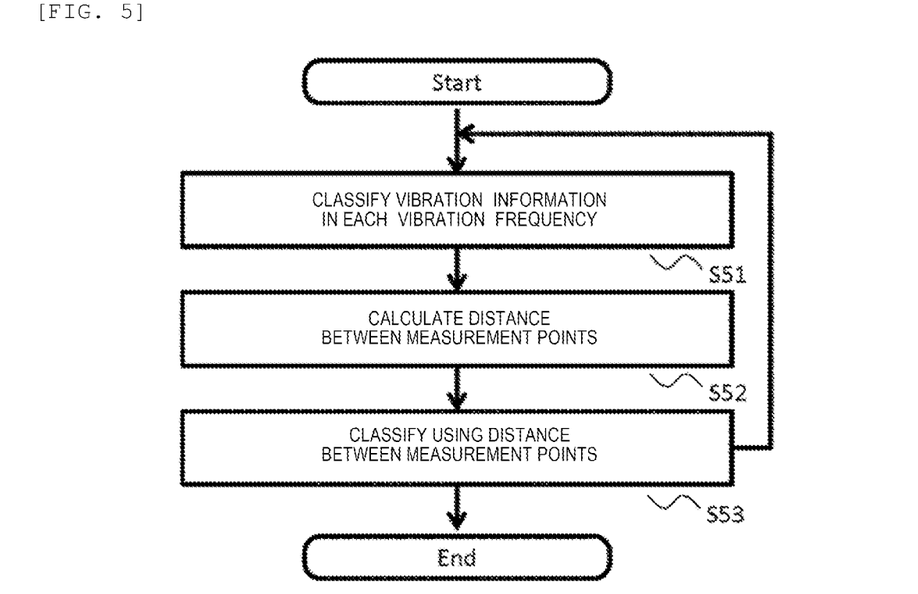
FIG. 5 is an example of a flow chart of a vibration information classification processing of the system stability monitoring apparatus.

An example of a detailed processing of a point clustering in S32 is illustrated using a flow chart illustrated in FIG. 5.

First, the vibration information calculated by the vibration analyzing unit 12 is classified using the vibration frequency included in the vibration information (S51).

FIG. 4 (b) illustrates an example of a data configuration of the vibration information which is classified using the vibration frequency. In an example illustrated in FIG. 4(b), as the vibration information in which the vibration frequency is 0.18, No. 1 vibration in the measurement point PMU1, and No. 1 vibration in the measurement point PMU2 are classified. In the same way, as the vibration information in which the vibration frequency is 0.65, No. 2 vibration in the measurement point PMU1 is classified.

At this time, the vibration frequency being used for classifying may allow vibration information within a preset range to be the same. In the example illustrated in FIGS. 4(a) and 4(b), the vibration frequency of No. 1 vibration in the measurement point PMU2 calculated in the vibration analyzing unit 12 is 0.19, but in FIG. 4(b), No. 1 vibration in the measurement point PMU1 in which the vibration frequency is 0.18 is classified in the same. When the vibration frequency classifies vibration within a range of a preset value in the same, even when an error caused by noise is included in the vibration information calculated in each point, distribution inside the system of each vibration information can be accurately estimated. Here, a value of determining a range of the vibration frequency as the same classification may be set on the basis of the number of data of the measurement information using an input of vibration analysis.

Next, the distance between the measurement points is calculated by the point information stored in the information storage unit 30 (S52).

Figure 6:
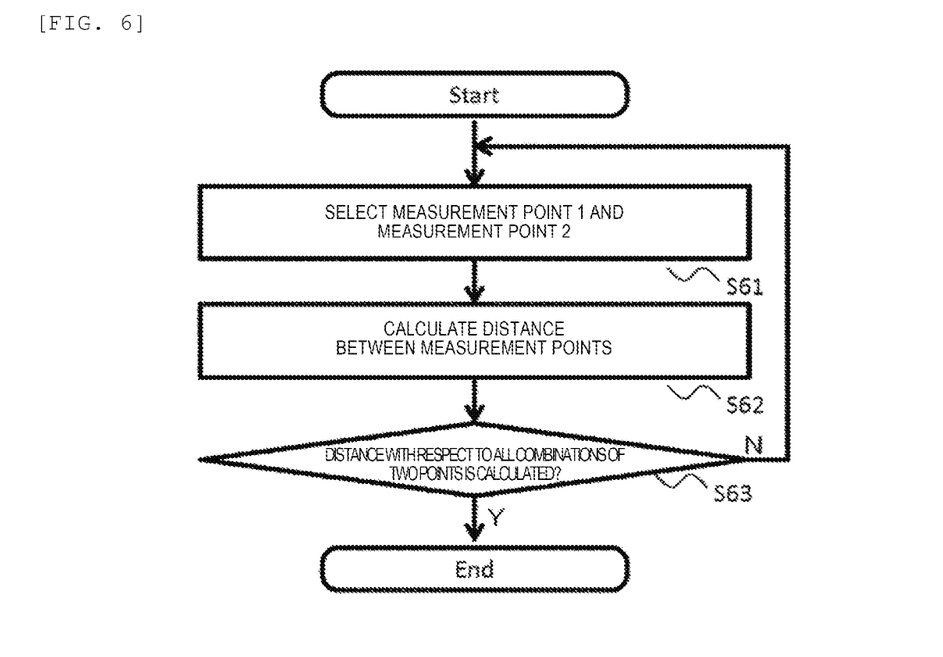
FIG. 6 is an example of a flow chart of a processing of calculating a distance between measurement points of the system stability monitoring apparatus.

FIG. 6 illustrates an example of a processing flow of a processing of calculating a distance between measurement points in S52.

The vibration classifying unit 13 selects two points from the measurement points at which the measurement information collecting unit 11 acquired the measurement information (S61).

Next, the distance between the measurement points between the two points selected in S61 is calculated based on the point information stored in the information storage unit 30 (S62).

Figure 7:
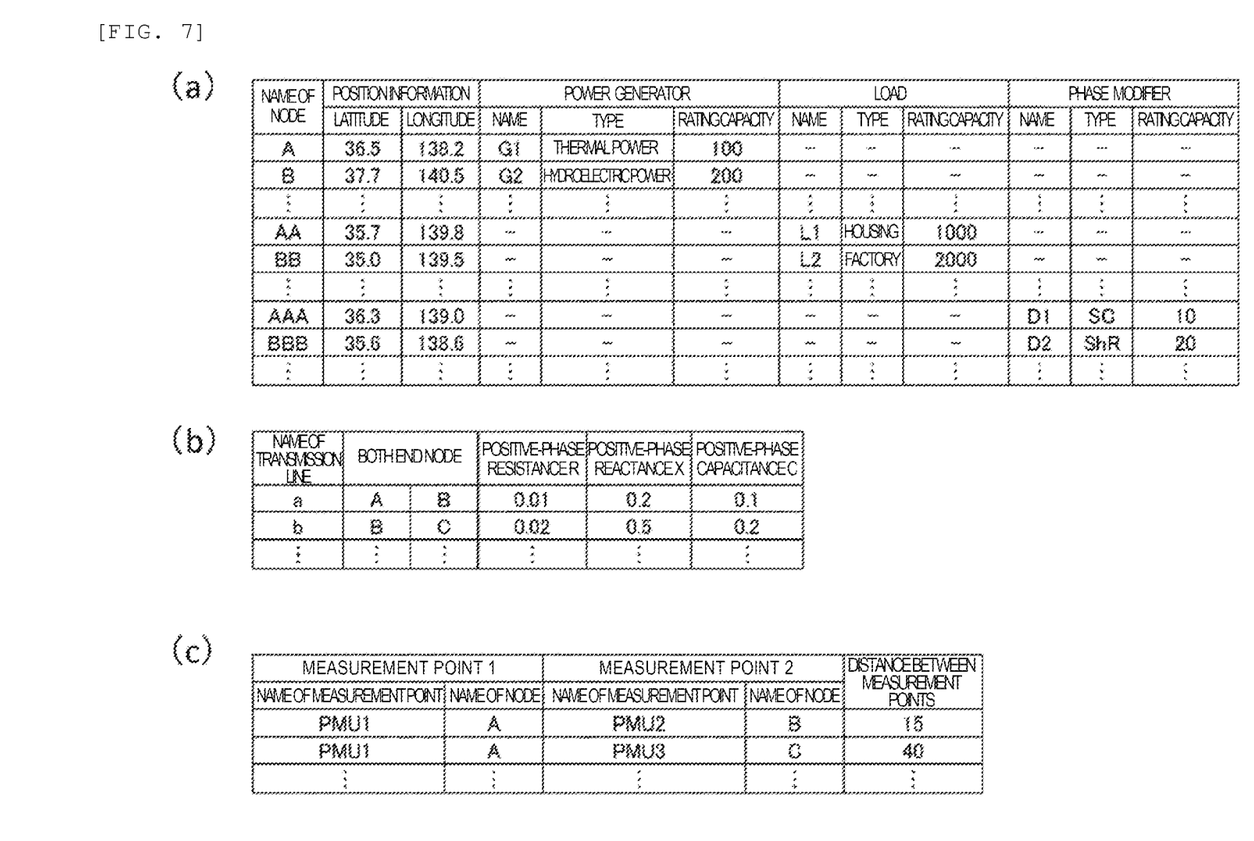
FIG. 7 is an example of a data configuration of point information input by the system stability monitoring apparatus.

FIG. 7 illustrates an example of a data configuration of the point information.

FIG. 7(a) illustrates an example of a node in the power system, and node information which indicates information of the power generator, the power load, and the phase modifier connected for each node. In an example of FIG. 7(a), the power generator is interconnected to a node which has a name A or B, and it is illustrated that a thermoelectric power generator of a rating capacity 100, which is referred to as a name of G1, is interconnected in the node A, and a wind power generator of a rating capacity 200, which is referred to as a name of G2, is interconnected in the node B. In addition, in the example of FIG. 7(a), the power load is interconnected to a node of a name of AA or BB, and it is illustrated that a housing of a rating capacity 1000, which is referred to as a name of L1, is interconnected in the node AA, and a factory of a rating capacity 2000, which is referred to as a name of L2, is interconnected in the node BB. In addition, in the example of FIG. 7(a), the phase modifier is interconnected to a node of a name of AAA and BBB, and it is illustrated that SC (power capacitor) of the rating capacity 10, which is referred to as a name of D1, is interconnected in the node AAA, and ShR (shunt reactor) of the rating capacity 20, which is referred to as a name of D2, is interconnected in the node BBB.

FIG. 7(b) illustrates an example of transmission line information which indicates characteristics of the transmission line in the power system. In an example of FIG. 7(b), the transmission line which has a name of a is present between the node A and the node B, and it is illustrated that a positive-phase resistance is 0.01, positive-phase reactance is 0.2, and positive-phase capacitance is 0.1.

FIG. 7(c) holds an example of the measurement point inside the power system, and the distance between the measurement points calculated in S62. Here, the measurement point indicates a point at which the measuring devices 21a and 21b are connected in FIG. 2. In the example of FIG. 7(c), the measurement point is indicated by a name of a node included in the node information of FIG. 7(a), and it is illustrated that a measurement point of a name of the measurement point, which is referred to as PMU1, is connected to the node A, and a measurement point of a name of the measurement point, which is referred to as PMU2, is connected to the node B. In addition, the distance between the measurement points indicates an electrical distance between two measurement points, and a value calculated on the basis of a system element of the power generator, the power load, the phase modifier, or the like which is interconnected to a vicinity of the two measurement points. For example, a distance D between the measurement points is calculated by Math. 13 to be described later.

$$D = \alpha d + \sum_{i=1}^{n} \beta_i C_i \qquad \text{[Math. 13]}$$

Here, d indicates an electrical distance proportional to an impedance between the two measurement points, n indicates the number of a system element such as the power generator, the power load, or the phase modifier interconnected within a range of an electrical distance, which is set at a certain threshold from either point of the two measurement points, $C_i$ indicates a rating capacity of an i-th system element interconnected within a range of an electrical distance, which is set at a certain threshold from any one of the two measurement points, and $\alpha$ and $\beta_i$ indicate a coefficient.

Here, the data configuration illustrated in FIGS. 7(a), (b), and (c) is an example, and may further store detailed point information. For example, as information of the node in which the thermoelectric power generator of FIG. 7(a) is interconnected, a dynamic characteristic of a governor constant number, or the like may be stored. In addition, as information of the node in which the power generator is interconnected by nature energy such as the wind power generator of FIG. 7(a), a stochastic power generating amount change characteristics calculated by a statistical analysis using a past history may be stored. In addition, in calculation of the distance between the measurement points of FIG. 7(c), a coefficient $\beta_i$ of (Expression 1) may be set on the basis of power generator dynamic characteristics. In addition, without using impedance or the information of a system element such as the power generator, the power load, or the phase modifier, using latitude and longitude information included in the node information of FIG. 7(a), a physical distance between the measurement points is calculated, and a value thereof may be set to be the distance D between the measurement points.

Next, in the measurement point acquiring the measurement information in the measurement information collecting unit 11, it is determined whether or not the distances between the measurement points with respect to all of combinations of two points is calculated (S63). In a case in which the distances between the measurement points with respect to all of the combinations of two points is calculated, a processing of calculating a distance between measurement points is terminated. In a case in which there is a combination of the measurement point where the distances between the measurement points is not calculated, S61 and S62 are repeated with respect to another two measurement points. By the above described processes, the distances between the measurement points with respect to all of the combinations of two measurement points are calculated.

Return to the description of the flow in FIG. 5.

The vibration information classified in each vibration frequency in S51 is classified using the distance between the measurement points calculated in S52 (S53). At this time, using the distance between the measurement points in every classification in S51, calculated in S52, the vibration information may be classified using a clustering method represented by a ward method, a k-means method.

FIG. 4(c) illustrates an example of a data configuration of the vibration information classified by the distance between the measurement points. Here, vibration observed in the measurement point PMU1 at the vibration frequency 0.18, and vibration observed in the measurement point PMU3 at the same vibration frequency 0.18 are classified as the other vibration in FIG. 4(c). This is because the distance between the measurement points of the measurement point PMU1 and the measurement point PMU3 is relatively great, and is classified to a separate group in a process of S53.

By the above described process, the vibration information calculated in the vibration analyzing unit 12 is classified using the point information stored in the information storage unit 30.

Figure 3:
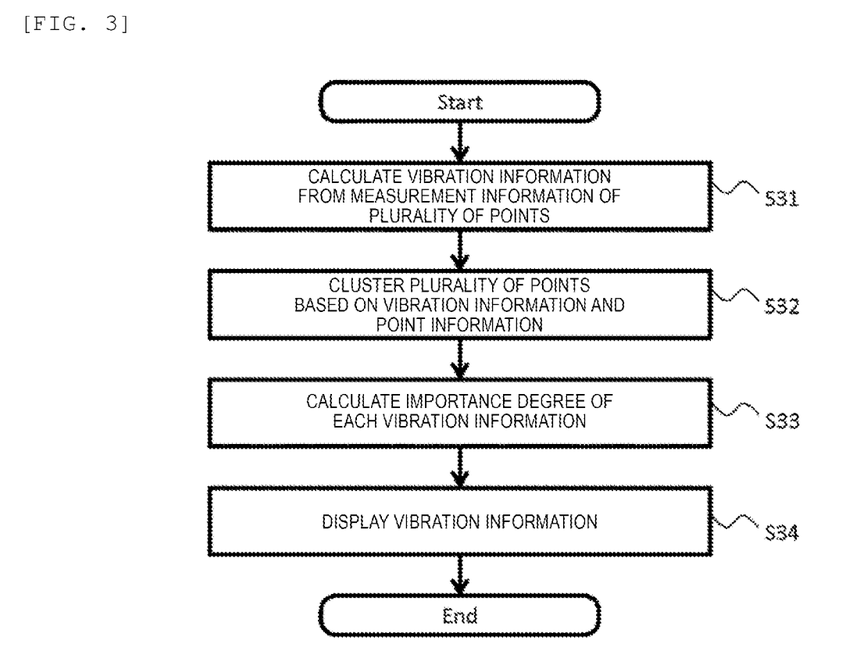
FIG. 3 is an example of a flow chart of a vibration classification processing of the system stability monitoring apparatus.

Return to the description of the flow of FIG. 3.

In S32, an importance degree is calculated in every vibration information classified using the point information (S33). Here, a value of Math. 14 to be described below is set to an importance degree, and the importance degree may be increased as the vibration has greater value.

$$S_i = \max_j (a_{ij} R_{ij}) + \max_j (b_{ij} \sigma_{ij}) \qquad \text{[Math. 14]}$$

Here, Si indicates an importance degree of i-th classification vibration, $R_{ij}$ indicates an amplitude of j-th vibration information included in the i-th classification, $\sigma_{ij}$ indicates an attenuation coefficient of the j-th vibration information included in the i-th classification, and $a_{ij}$ and $b_{ij}$ indicate a coefficient. An importance degree Si calculated by Math. 14 becomes a great value, as the amplitude of the vibration of the i-th classification is great and the attenuation coefficient is great. Since effects in all vibration components are increased as the amplitude of vibration is great, and a possibility of being diffused is high as the attenuation coefficient is increased to be unstabilized, the system stability can be monitored by preferentially monitoring vibration in which the importance degree Si is great.

In addition, an importance degree Si may be calculated using the past vibration information. For example, in the past vibration information, in a case in which vibration including the vibration frequency continuously same or slightly changed in a period or more determined by a certain threshold is present, an importance degree Si is great, and in a case in which vibration including the vibration frequency continuously same or slightly changed in only a period of the threshold or less, the importance degree Si may be set to be small. When the importance degree Si is determined as described above, vibration due to an effect of noise which is instantaneously included in system vibration is removed, and the vibration information which is normally present can be preferentially monitored.

An importance degree in each of the vibration information calculated and classified in S31 and S32, and the vibration information calculated in S33 is displayed (S34).

Figure 8:
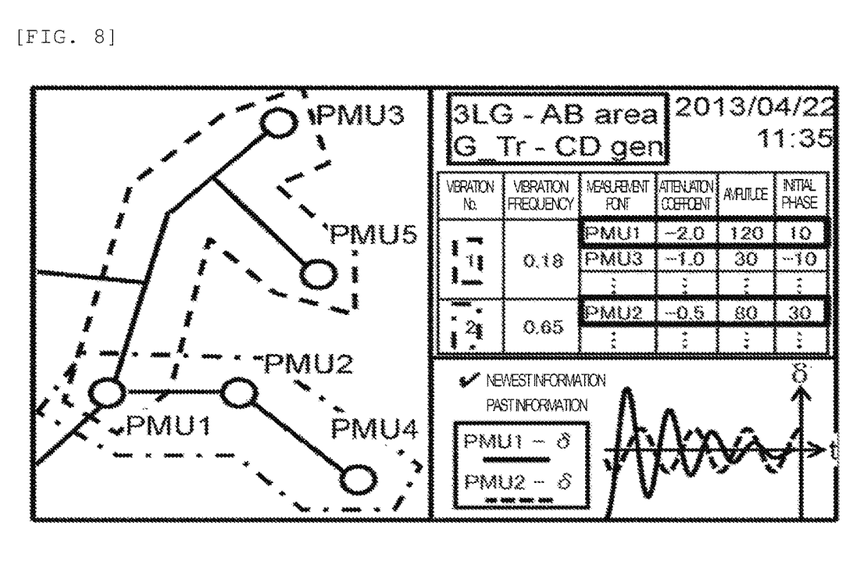
FIG. 8 is an example of a configuration of display screen of the system stability monitoring apparatus.

FIG. 8 illustrates an example of a display screen in the system stability monitoring apparatus.

The vibration information in which the importance degree is high calculated in S33 is displayed, and based on the vibration information calculated and classified in S31 and S32, the measurement point colored in every classification is displayed on the system diagram. In an example of FIG. 8, the system diagram and the measurement points PMU1 to PMU5 are displayed on a left side of a screen. Further, based on the vibration information calculated and classified in S31 and S32, the measurement point corresponding to each vibration in a region surrounded by a broken line or a dashed line is illustrated. In addition, a detail of each vibration information calculated and classified in S31 and S32, failure information of ground-circuit and short circuit generated in a vicinity area which affects wide vibration phenomenon, and the power generator drop-out information are displayed on a right side of the screen of FIG. 8. The vibration information which indicates the detail with high importance degree calculated in S33 is preferentially displayed. Further, measurement points selected by an operator are displayed on the lower right side of the screen of FIG. 8 and the time-series data of the measurement information for different types is displayed in the graph in FIG. 8. The operator can select and display newest information and past information as a display time zone of the time-series data. In addition to a display example illustrated in FIG. 8, the vibration frequency included in the vibration information and the time-series data of the attenuation coefficient may be displayed.

REFERENCE SIGNS LIST 10 system stability calculating unit
11 measurement information collecting unit
12 vibration analyzing unit
13 vibration classifying unit
21 system measuring unit
30 information storage unit
101 power generator
102 substation
103 phase modifier
104 power load
105 external power system
106 information communication network
200 system stability monitoring apparatus
201 CPU
202 display device
203 communication means
204 input means
205 memory
206 storage device

The invention claimed is:

1. A system stability monitoring apparatus which monitors system stability of a power system comprising:
a measurement information collecting unit that collects measurement information of a plurality of points in the power system at a plurality of times;
a vibration analyzing unit that calculates vibration information at the plurality of points using the measurement information, the vibration information including a plurality of vibration frequencies, a plurality of attenuation coefficients, a plurality of amplitudes, and a plurality of initial phases;
an information storage unit that stores point information including position information for each of the plurality of points;
a vibration classifying unit that classifies the vibration information as a plurality of vibrations based on the point information to distinguish the plurality of vibrations at the plurality of points, where each of the vibrations includes at least one of the respective vibration frequencies, one or more points corresponding to at least one of the respective vibration frequencies, and respective attenuation coefficients, respective amplitudes and respective initial phases corresponding to the one or more of the points corresponding to the at least one of the respective vibration frequencies, and
the vibration classifying unit calculates a respective importance degree for each of the plurality of vibrations based on the respective amplitudes and the respective attenuation coefficients thereof; and
a display unit that displays the vibration information for at least a first vibration and a second vibration of the plurality of vibrations and displays a system diagram of the power system which includes a first region indicating the one or more points corresponding to the first vibration and a second region indicating the one or more points corresponding to the second vibration,
wherein the respective importance degree for the first vibration and the respective importance degree for the second vibration are higher than a predetermined value,
wherein the vibration classifying unit classifies the at least one of the respective vibration frequencies in a predetermined range as a same one of the vibrations.

2. The system stability monitoring apparatus according to claim 1,
wherein the respective importance degree is calculated for each of the plurality of vibrations according to the equation:

$$S_i = \max_j (a_{ij} R_{ij}) + \max_j (b_{ij} \sigma_{ij}),$$

where $S_i$ is the respective importance degree of an i-th vibration, $R_{ij}$ is a j-th amplitude of the i-th vibration, $\sigma_{ij}$ is a j-th attenuation coefficient of the i-th vibration and $a_{ij}$ and $b_{ij}$ are predetermined coefficients.

3. The system stability monitoring apparatus according to claim 1,
wherein, based on past vibration information, the vibration classifying unit increases the respective importance degree in a case in which a change of the vibration information thereof is continuous over a predetermined period, or lowers the respective importance degree in a case in which the change of the vibration information thereof is not continuous over the predetermined period.

4. The system stability monitoring apparatus according to claim 1,
wherein the vibration analyzing unit calculates the vibration information using any one method of a Fourier analysis, a wavelet analysis, a Purony's method, a Matrix Pencil method, and a Hankel Total Least Squares (HTLS) method.

5. The system stability monitoring apparatus according to claim 1,
wherein the first region includes at least one point which is also included in the second region.

6. The system stability monitoring apparatus according to claim 5,
wherein the display unit displays the vibration information for at least the first vibration and the second vibration on a priority basis.

7. A system stability monitoring apparatus which monitors system stability of a power system comprising:
a measurement information collecting unit that collects measurement information at a plurality of points in the power system at a plurality of times, where each of the points is associated with a respective power generator, a respective load, or a respective phase modifier;

a vibration analyzing unit that calculates vibration information at the plurality of points using the measurement information, the vibration information including a plurality of vibration frequencies, a plurality of attenuation coefficients, a plurality of amplitudes, and a plurality of initial phases;

an information storage unit that stores point information including position information for each of the plurality of points;

a vibration classifying unit that classifies the vibration information as a plurality of vibrations based on the point information to distinguish the plurality of vibrations at the plurality of points, where each of the vibrations includes a respective vibration frequency, one or more points corresponding to the respective vibration frequency, and respective attenuation coefficients, respective amplitudes and respective initial phases corresponding to the one or more of the points corresponding to the respective vibration frequency; and a display unit that displays the vibration information for at least a first vibration and a second vibration of the plurality of vibrations and displays a system diagram of the power system which includes a first region indicating the one or more points corresponding to the first vibration and a second region indicating the one or more points corresponding to the second vibration, wherein the point information includes at least one of latitude information and longitude information of each the plurality of points, impedance information between the plurality of points, and characteristic information of at least one of the respective power generator, the respective load, and the respective phase modifier associated with the each of the plurality of points.

8. The system stability monitoring apparatus according to claim 7, wherein, based on the impedance information and the characteristic information, the vibration classifying unit calculates a plurality of electrical distances between the plurality of points, and classifies the vibration information as the plurality of vibrations based on the plurality of electrical distances.

9. The system stability monitoring apparatus according to claim 7, wherein, based on the latitude information and longitude information of each the plurality of points, the vibration classifying unit calculates a plurality of physical distances between the plurality of points, and classifies the vibration information as the plurality of vibrations based on the plurality of physical distances.

10. A system stability monitoring method which monitors system stability of a power system comprising:

collecting measurement information of a plurality of points in the power system at a plurality of points;

calculating vibration information at the plurality of points using the measurement information, the vibration information including a plurality of vibration frequencies, a plurality of attenuation coefficients, a plurality of amplitudes, and a plurality of initial phases; and classifying the vibration information as a plurality of vibrations based on point information, that includes geographic position information for each of the plurality of points, to distinguish the plurality of vibrations at the plurality of points, where each of the vibrations includes at least one of the respective vibration frequencies, one or more points corresponding to the at least one of the respective vibration frequencies, and respective attenuation coefficients, respective amplitudes and respective initial phases corresponding to the one or more of the points corresponding to the at least one of the respective vibration frequencies;

calculating a respective importance degree for each of the plurality of vibrations based on the respective amplitudes and the respective attenuation coefficients thereof; and displaying the vibration information for at least a first vibration and a second vibration of the plurality of vibrations and a system diagram of the power system which includes a first region indicating the one or more points corresponding to the first vibration and a second region indicating the one or more points corresponding to the second vibration, wherein the respective importance degree for the first vibration and the respective importance degree for the second vibration are higher than a predetermined value.

11. The system stability monitoring method according to claim 10, wherein the point information includes at least one of latitude information and longitude information of each the plurality of points, impedance information between the plurality of points, and characteristic information of at least one of the respective power generator, the respective load, and the respective phase modifier associated with the each of the plurality of points.

12. The system stability monitoring apparatus according to claim 11, further comprising:

calculating a plurality of electrical distances between the plurality of points based on the impedance information and the characteristic information, and wherein the vibration information is classified as the plurality of vibrations based on the plurality of electrical distances.

13. The system stability monitoring apparatus according to claim 11, further comprising:

calculating a plurality of physical distances between the plurality of points based on the latitude information and longitude information of each the plurality of points, wherein the vibration information is classified as the plurality of vibrations based on the plurality of physical distances.

* * * * *